United States Patent [19]

Hauck et al.

[11] 4,003,930
[45] Jan. 18, 1977

[54] 2,3-TRANS-5-[3-(AMINO)-2-HYDROXY-PROPOXY]-1,2,3,4-TETRAHYDRO-3-(OR 2)-AMINO-2-(OR 3)-HYDROXY-NAPHTHALENES AND SALTS THEREOF

[75] Inventors: Frederic P. Hauck, Somerville; Christopher M. Cimarusti, Hamilton, both of N.J.; Joseph E. Sundeen, Yardley, Pa.

[73] Assignee: E. R. Squibb & Sons, Inc., Princeton, N.J.

[22] Filed: Feb. 28, 1974

[21] Appl. No.: 446,859

Related U.S. Application Data

[63] Continuation-in-part of Ser. No. 268,301, July 3, 1972, abandoned.

[52] U.S. Cl. .................. 260/570.7; 260/343.7; 260/348 R; 260/348 C; 260/348.5 R; 260/349; 260/479 R; 260/501.18; 260/501.19; 260/567.6 M; 260/567.68; 260/570.8 R; 260/575; 424/280; 424/316; 424/329; 424/330
[51] Int. Cl.$^2$ ......................................... C07C 93/06
[58] Field of Search ............... 260/570.7, 567.6 M, 260/501.18, 501.19, 343.7; 424/329, 330

[56] References Cited

UNITED STATES PATENTS 3,935,267  1/1976  Hauck et al. .................. 260/570.7

*Primary Examiner* — Robert V. Hines
*Attorney, Agent, or Firm* — Lawrence S. Levinson; Merle J. Smith; Donald J. Barrack

[57] ABSTRACT

This invention relates to novel cyclic polymethylene phenoxy-aminopropanols having the structure

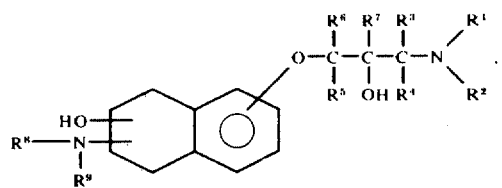

and the pharmaceutically acceptable salts of said compounds, wherein $R^1$, $R^2$, $R^8$ and $R^9$ are each independently selected from hydrogen, lower alkyl and aryl-lower alkyl and $R^3$, $R^4$, $R^5$, $R^6$ and $R^7$ are each independently selected from hydrogen and lower alkyl, which are useful in the treatment of coronary diseases.

9 Claims, No Drawings

2,3-TRANS-5-[3-(AMINO)-2-HYDROXY-PROPOXY]-1,2,3,4-TETRAHYDRO-3-(OR 2)-AMINO-2-(OR 3)-HYDROXY-NAPHTHALENES AND SALTS THEREOF

This application is a continuation-in-part of copending U.S. patent application Ser. No. 268,301, filed July 3, 1972, now abandoned.

BRIEF DESCRIPTION OF THE INVENTION

This invention relates to novel chemical compounds of the formula

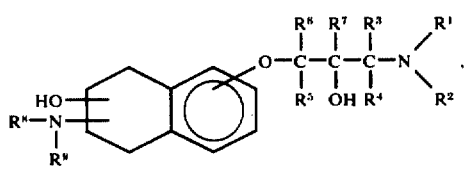

and pharmaceutically acceptable salts thereof, where $R^1$, $R^2$, $R^8$ and $R^9$ can each be hydrogen, lower alkyl and aryl-lower alkyl and $R^3$, $R^4$, $R^5$, $R^6$ and $R^7$ can be hydrogen or lower alkyl.

The term "lower alkyl" as employed herein refers to both straight and branched chain radicals of up to and including eight carbon atoms, for instance, methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl and the like; alkyl groups of one to four carbon atoms are preferred.

The term "aryl" as employed herein refers to phenyl and phenyl substituted with lower alkyl, halogen, or nitro.

The term "aryl-lower alkyl" as employed herein refers to a lower alkyl group (as defined above) substituted with an aryl group (as defined above). Included among the aryl-lower alkyl groups are benzyl and phenethyl.

The term "halogen" as employed herein refers to fluorine, chlorine, bromine, and iodine; chlorine and bromine are preferred.

DETAILED DESCRIPTION OF THE INVENTION

The compounds of this invention are useful as antifibrillatory agents, for example, in arresting cardiac arrhythmia in mammals, e.g., by inhibition of beta adrenergic receptors in the myocardium. For these purposes a compound of formula I, or a physiologically acceptable acid-addition salt thereof, may be incorporated in a conventional dosage form such as tablet, capsule, elixir, injectable or the like along with the necessary carrier material, excipient, lubricant, buffer or the like. Single or divided doses of about 5 to 25 mg/kg/day, preferably about 4 to 10 mg/kg, two to four times daily may be administered in dosage forms as described above.

The compounds of formula I form acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Then any other salt may again be formed from the free base and the appropriate inorganic or organic acid. Illustrative are the hydrohalides, especially the hydrochloride and hydrobromide which are preferred, sulfate, nitrate, phosphate, borate, acetate, tartrate, maleate, citrate, succinate, benzoate, ascorbate, salicylate, methanesulfonate, benzenesulfonate, toluenesulfonate and the like. Quaternary ammonium salts are also formed, e.g., by reacting the free base with an alkylating agent, e.g., lower alkyl halide such as methyl chloride, ethyl bromide or the like, lower alkyl sulfate such as methyl sulfate, aralkyl halides such as benzyl chloride, aralkyl sulfates such as benzyl sulfate and the like.

Compounds of formula I can be prepared using compounds of the structure

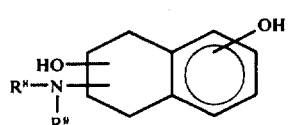

as starting materials. The compounds of formula II are described in copending U.S. patent application Ser. No. 268,314, filed July 3, 1972 entitled, "Substituted Cyclic Polymethylene Phenols" and now abandoned.

Reaction of a compound of formula II with an alkali metal alkoxide, such as $NaOCH_3$, in an alcohol solvent boiling below 100° C, such as methanol and removing the solvent in vacuo gives a dry salt. The dry salt is reacted with an epoxide having the structure

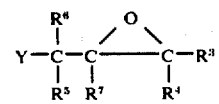

wherein Y is chlorine or bromine, such as epichlorohydrin, in a solvent such as dimethylsulfoxide, to yield a 1,2,3,4-tetrahydro-5-[2,3-epoxy-propoxy]-naphthalene of the structure

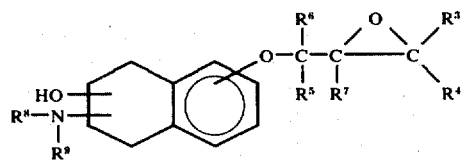

An epoxy-propoxy-naphthelene of formula IV can be converted to a compound of formula I by heating it with an amine of the formula

in an inert organic solvent, such as n-propanol, benzene or toluene, e.g., for about 16 to 24 hours; the reactants may also be heated in a Parr pressure reactor at a temperature within the range of from about 70° to about 110° C for 6 to 12 hours.

Alternatively, compounds of formula I can be prepared by reacting a salt of a starting material of formula II with a compound having the structure

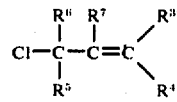

to form an ether having the structure

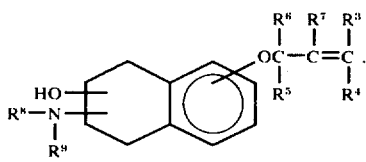

An ether of formula VII can be epoxidized by reaction with a suitable oxidizing agent, such as m-chloroperbenzoic acid or other peracid, in a solvent such as chloroform, to form compounds of formula IV. The epoxy-propoxy-naphthalene of formula IV can then be used to form a compound of formula I in the manner described above. This method is particularly applicable wherein $R^3$, $R^4$ and/or $R^7$ are other than hydrogen and $R^5$ and $R^6$ are hydrogen.

Compounds of formula I wherein $R^3$, $R^4$, $R^5$, $R^6$ and $R^7$ are all hydrogen are preferred.

Compounds of formula I wherein $R^1$ is hydrogen or lower alkyl and $R^2$ is lower alkyl are preferred. Compounds of formula I wherein $R^1$ is hydrogen are especially preferred.

The following examples are specific embodiments of this invention.

EXAMPLE 1

2,3-trans-5-[3-(Isopropylamino)-2-hydroxypropoxy]-1,2,3,4-tetrahydro-3-(or 2)-(isopropylamino)-2-(or 3)-hydroxy-naphthaline A. 6,7-Epoxy-5,6,7,8-tetrahydro-1-naphthol acetate A solution of 101 g (0.542 M) of 5,8-dihydro-1-naphthol acetate in 1.5 liters of methylene chloride is cooled to 0° C and 89 g (0.516 M) of m-chloroperbenzoic acid is added over a period of 5 minutes. The mixture is stirred overnight at room temperature.

The suspension is poured into a mixture of 500 ml of 10% sodium hydroxide and 1000 g of ice. The aqeuous layer is extracted with methylene chloride (two 500 ml portions), and the combined organic layers are washed with water and saturated sodium chloride solution, dried and evaporated in vacuo to give the title compound, 105 g of pink solid.

B. 6,7-trans-5,6,7,8-Tetrahydro-7(and 6)-(isopropylamino)-1,6(and 7)-naphthalenediol A mixture of 10.7 g (0.05 M) of the above epoxy acetate and 50 ml of isopropylamine is heated in a bomb at 100° C overnight. Removal of excess amine leaves a viscous material that is chromatographed on 500 g of neutral alumina (Activity III). 10–20% Methanol in chloroform elutes the desired product. The product (a mixture of the above isomers) is crystallized from ether and found to have a melting point of 112°–117° C. The hydrochloride salt has a melting point of 207°–210° C.

C. 2,3-trans-5-[3-(Isopropylamino)-2-hydroxypropoxyl-1,2,3,4-tetrahydro-3-(or 2)-(isopropylamino)-2-(or 3)-hydroxy-naphthalene A solution of 6,7-trans-5,6,7,8-tetrahydro-7(and 6)-(isopropylamino)-1,6(and 7)-naphthalenediol and sodium methoxide in methanol is prepared and the solvent is then removed in vacuo. The residue is stirred overnight with epichlorohydrin in dimethylsulfoxide under nitrogen. The dimethylsulfoxide is removed in vacuo and the residue is dissolved in chloroform, washed with water, dried and evaporated. The resulting material is heated at 80° C ± 5° overnight with isopropylamine to yield the title compound.

EXAMPLE 2 trans-5-[3-(tert-Butylamino)-2-hydroxy-2-methyl-propoxyl]-1,2,3,4-tetrahydro-2-(isopropylamino)-3-hydroxy-naphthalene A. 6,7-Epoxy-5,6,7,8-tetrahydro-1-naphthol acetate A solution of 101 g (0.542 M) of 5,8-dihydro-1-naphthol acetate in 1.5 liters of methylene chloride is cooled to 0° C and 89 g (0.516 M) of m-chloroperbenzoic acid is added over a period of 5 minutes. The mixture is stirred overnight at room temperature.

The suspension is poured into a mixture of 500 ml of 10% sodium hydroxide and 1000 g of ice. The aqueous layer is extracted with methylene chloride (two 500 ml portions), and the combined organic layers are washed with water and saturated sodium chloride solution, dried and evaporated in vacuo to give the title compound, 105 g of pink solid.

B. 6,7-trans-5,6,7,8-Tetrahydro-7(and 6)-(isopropylamino)-1,6(and 7)-naphthalenediol, hydrochloride A mixture of epoxy acetate (10. 2 g; 0.05 M) and isopropylamine is charged to a small bomb and heated overnight in an oil bath maintained at 100° C. After cooling, the excess amine is removed in vacuo leaving a dark brown viscous material which is chromatographed on neutral alumina (Activity III). Fractions eluted with 10–20% methanol in chloroform yield crystalline material on standing under hexane. Two recrystallizations from ether give a sample having a melting point of 112°–117° C. This is dissolved in isopropanol-ether and converted to the hydrochloride by adding a solution of HCl in isopropanol. The white hydrochloride is recrystallized from isopropanol-methanol-ether to give 2.2 g of the title isomers, melting point 207°–210° C.

Anal. Calc'd. for $C_{13}H_{20}O_2NCl$:

C, 60.57; H, 7.82; N, 5.43; Cl, 13.75.

Found: C, 60.81; H, 7.72; N, 5.24; Cl, 13.61.

C. 2-Methyl-3-[trans-7(or 6)-(isopropylamino)-6(or 7)-hdyroxy-5,6,7,8-tetrahydro-1-naphthoxy]-1-propene A solution of 9.0 g (0.05 mole) of 6,7-trans-5,6,7,8-tetrahydro-7(or 6)-(isopropylamino)-1,6(or 7)-naphthalenediol and 2.7 g (0.05 mole) of sodium methoxide is prepared in 200 ml of methanol and the solvent is removed in vacuo. The residue is dissolved in 120 ml of dimethylsulfoxide, 20 ml distilled out at 40° C at 0.2 mm, and the resulting solution stirred for 4 hours under nitrogen with 6.3 g (0.07 mole) of β-methallyl chloride. The bulk of the dimethylsulfoxide is removed in vacuo and the residue is triturated with 200 ml of ice water.

The resulting solid is filtered, dissolved in chloroform, dried and the solvent removed to give the title compound.

D. 2-Methyl-3-[trans-7(or 6)-(isopropylamino)-6(or 7)-hydroxy-5,6,7,8-tetrahydro-1-naphthoxy]-1,2-epoxy-propane A solution of 7.5 g (0.033 mole) of 2-methyl-3-[trans-7(or 6)-(isopropylamino)-6(or 7)-hydroxy-5,6,7,8-tetrahydro-1-naphthoxy]-1-propene in 220 ml of dichloromethane is allowed to stand at room temperature with 7.0 g of m-chloroperbenzoic acid. The resulting slurry is extracted with cold sodium hydroxide solution, dried and evaporated to give the title compound.

E. trans-5-[3-(tert-Butylamino)-2-hydroxy-2-methylpropoxy]-1,2,3,4-tetrahydro-2-(isopropylamino)-3-hydroxynaphthalene A mixture of 5.2 g of 2-methyl-3-[trans-7(or 6)-(isopropylamino)-6(or 7)-hydroxy-5,6,7,8-tetrahydro-1-naphthoxy]-1,2-epoxypropane and 50 ml of t-butyl amine is heated at 80° C ±5° for 17 hours in a small Parr bomb. Solvent removal gives an oil. A solution of this oil in acetonitrile crystallizes after 2 weeks at −20° C. Two recrystallizations from ether gives the title compound.

EXAMPLE 3 trans-5-[3-(tert-Butylamino)-2-hydroxy-2-methylpropoxy]-1,2,3,4-tetrahydro-2-hydroxy-3-(benzylmethylamino)-naphthalene A. trans-6(and 7)-(Benzylmethylamino)-5,6,7,8-tetrahydro-1,7(and 6)-naphthalenediol A mixture of 6,7-epoxy-5,6,7,8-tetrahydro-1-naphthol acetate (10.2 g. 0.05 M), prepared as described in Example 1A, methylbenzylamine (50 g) and xylene (50 ml) is heated under reflux overnight. After cooling, the solution is taken to dryness in vacuo and the dark brown viscous material remaining is chromatographed on silica gel (Davison Grade 923, 100–200 mesh). Fractions eluted with 1–5% methanol in chloroform, containing 11.0 g (ca. 76%), show a single spot on TLC (silica gel, developed with 2% methanol in chloroform). Ether is added to these fractions, and after standing, a small amount of crystalline material is deposited. This is harvested (1.6 g) and recrystallized from ether to give the title compound 1.15 g, melting point 152°–154° C.

Anal. Calc'd. for $C_{18}H_{21}O_2N$: C, 76.29; H, 7.47; N, 4.94.

Found: C, 76.24; H, 7.69; N, 4.75.

B. 2-Methyl-3-[trans-6(or 7)-(benzylmethylamino)-6(or 7)-hydroxy-5,6,7,8-tetrahydro-1-naphthoxy]-1-propene A solution of 9.0 g (0.05 mole) of trans-6(or 7)-(benzylmethylamino)-5,6,7,8-tetrahydro-1,7(or 6)-naphthalenediol and 2.7 g (0.05 mole) of sodium methoxide is prepared in 200 ml of methanol and the solvent removed in vacuo. The residue is dissolved in 120 ml of dimethylsulfoxide, 20 ml distilled out at 40° C at 0.2 mm, and the resulting solution stirred for 4 hours under nitrogen with 6.3 g (0.07 mole) of β-methallyl chloride. The bulk of the dimethylsulfoxide is removed in vacuo and the residue is triturated with 200 ml of ice water. The resulting solid is filtered, dissolved in chloroform, dried and the solvent removed to give the title compound.

C. 2-Methyl-3-[trans-6(or 7)-(benzylmethylamino)-7(or 6)-hydroxy-5,6,7,8-tetrahydro-1-naphthoxy]-1,2-epoxypropane A solution of 7.5 g (0.033 mole) of 2-methyl-3-[trans-6(or 7)-(benzylmethylamino)-6(or 7)-hydroxy-5,6,7,8-tetrahydro-1-naphthoxy]-1-propane in 220 ml of dichloromethane is allowed to stand at room temperature overnight with 7.0 g of m-chloroperbenzoic acid. The resulting slurry is extracted with cold sodium hydroxide solution, dried and evaporated to give the title compound.

D. trans-5-[3-(tert-Butylamino)-2-hydroxy-2-methylpropoxy]-1,2,3,4-tetrahydro-2-hydroxy-3-(benzylmethylamino)-naphthalene A mixture of 5.2 g of 2-methyl-3-[trans-6(or 7)-(benzylmethylamino)-7(or 6)-hydroxy-5,6,7,8-tetrahydro-1-naphthoxy]-1,2-epoxypropane and 50 ml of t-butylamine is heated at 80° C±5° for 17 hours in a small Parr bomb. Solvent removal gives an oil. A solution of this oil in acetonitrile crystallizes after 2 weeks at −20° C. Two recrystallizations from ether give the title compound.

EXAMPLE 4 trans-5-[3-(tert-Butylamino)-2-hydroxy-2-methylpropoxy]-1,2,3,4-tetrahydro-2-hydroxy-3-amino-naphthalene trans-6(and 7)-Amino-5,6,7,8-tetrahydro-1,7(and 6)-naphthalenediol A solution of 6,7-epoxy-5,6,7,8-tetrahydro-1-naphthol acetate (20.4 g, 0.1 M), prepared as described in Example 1A, in 200 ml dioxane is heated to 40° C and a solution of sodium azide (6.8 g, 0.11 M) in water (20 ml) is added dropwise. The mixture is heated under reflux overnight, cooled, filtered and the solvent is removed in vacuo.

The crude azide is dissolved in ethanol, platinum oxide (ca. 1g) is added and the mixture is hydrogenated at up to 45 psi for 20 hours. During this time the bottle is vented and refilled with hydrogen six times. The catalyst is removed by filtration and washed with ethanol. The filtrate is taken to dryness in vacuo, hexane is added and crystalline product is removed by filtration (13.1 g). A 3.0 g sample of this is recrystallized twice from ethyl acetate methanol to give the title compound, 1.5 g, melting point 172°–193° C, dec.

Anal. Calc'd. for $C_{10}H_{13}NO_2$: C, 67.02; H, 7.31, N, 7.82.

Found: C, 67.24; H, 7.33; N, 7.84.

B. 2-Methyl-3-(trans-6(or 7)-amino-7-amino-7(or 6)-hydroxy-5,6,7,8-tetrahydro-1-naphthoxy)-1-propene A solution of 9.0 g (0.05 mole) of trans-6(or 7)-amino-5,6,7,8-tetrahydro-1,7(or 6)-naphthalenediol and 2.7 g (0.05 mole) of sodium methoxide is prepared in 200 ml of methanol and the solvent removed in vacuo. The residue is dissolved in 120 ml of dimethylsulfoxide, 20 ml distilled out at 40° C at 0.2 mm, and the resulting solution is stirred for 4 hours under nitrogen with 6.3 g (0.07 mole) of β-methallyl chloride. The bulk of the dimethylsulfoxide is removed in vacuo and the residue is triturated with 200 ml of ice water. The resulting solid is filtered, dissolved in chloroform, dried and the solvent removed to give the title compound.

C. 2-Methyl-3-[trans-6(or 7)-amino-6(or 7)-hydroxy-5,6,7,8-tetrahydro-1-naphthoxy]-1,2-epoxypropane A solution of 7.5 g (0.033 mole) of 2-methyl-3-(trans-6(or 7)-amino-7(or 6)-hydroxy-5,6,7,8-tetrahydro-1-naphthoxy)-1-propene in 220 ml of dichloromethane is allowed to stand at room temperature overnight with 7.0 g of m-chloroperbenzoic acid. The resulting slurry is extracted with cold sodium hydroxide solution, dried and evaporated to give the title compound.

D. trans-5-[3-(tert-Butylamino)-2-hydroxy-2-methylpropoxy]-1,2,3,4-tetrahydro-2-hydroxy-3-aminonaphthalene A mixture of 5.2 g of 2-methyl-3-[trans-6(or 7)-amino-6(or 7)-hydroxy-5,6,7,8-tetrahydro-1-naphthoxy]-1,2-epoxypropane and 50 ml of t-butylamine is heated at 80° C±5° for 17 hours in a small Parr bomb. Solvent removal gives an oil. A solution of this oil in acetonitrile crystallizes after 2 weeks at −20° C. Two recrystallizations from ether give the title compound.

EXAMPLE 5

2,3-trans-5-[3-(tert-Butylamino)-2-hydroxypropoxy]-1,2,3,4-tetrahydro-2-hydroxy-3-methylamino-naphthalene and the 8-isomer A. 5,8-Dihydro-1-naphthol, benzyl ether A solution of 5,8-dihydro-1-naphthol (73 g, 0.5 M) in 400 ml dimethylsulfoxide is treated with 0.5 M of sodium methoxide. The mixture is cooled in an ice bath while benzyl bromide (85.5 g, 0.5 M) is added dropwise. The mixture has to be shaken periodically since there is difficulty in stirring. Toward the end of the addition the mixture is allowed to warm to ca. 45° C, and stirring is continued for 2–3 hours after addition is complete. The mixture is then poured into 1 liter of water and the product is extracted into ether. The ether extracts are washed with 10% sodium hydroxide and the solvent is removed in vacuo to give a quantitative yield of crude crystalline product.

A small sample (4 g) of this is recrystallized twice from methanol to give the benzyl ether, 1.3 g, melting point 70°–74° C.

Anal. Calc'd. for $C_{17}H_{16}O$: C, 86.40; H, 6.83.
Found: C, 86.58; H, 6.60.

B. 6,7-Epoxy-5,6,7,8-tetrahydro-1-naphthol, benzyl ether

The dihydro benzyl ether (47 g, 0.2 M) is dissolved in 200 ml chloroform and treated with a chloroform solution of 50 g of m-chloroperbenzoic acid which is added dropwise over a period of 1 hour. The mixture is stirred overnight at room temperature. A small amount of insoluble material is then removed by filtration and the filtrate is poured into a dilute potassium carbonate solution. After stirring a few minutes the layers are separated and the chloroform solution is dried over potassium carbonate, filtered, and the solvent is removed in vacuo leaving a quantitative yield of crude epoxide.

C. trans-3-(Benzylmethylamino)5(and 8)-benzyloxy-1,2,3,4-tetrahydro-2-naphthol

A mixture of the crude epoxide (10 g, 0.042 M) and methylbenzylamine (35 g) in 125 ml toluene is heated under reflux overnight. After cooling, the reaction mixture is taken to dryness in vacuo leaving 15.2 g of dark brown oil. This is chromatographed on neutral alumina (Activity II). Fractions eluted with benzene-chloroform and chloroform crystallize on standing. These contain 6.0 g of material. Part of this material is recrystallized twice from ether to give the title compound, 400 mg, melting point 126°–136° C.

D. trans-3-(Methylamino)-5(and 8)-hydroxy-1,2,3,4-tetrahydro-2-naphthol trans-3-(Benzylmethylamino)-5(and 8)-benzyloxy-1,2,3,4-tetrahydro-2-naphthol is catalytically debenzylated over 5% Pd on charcoal in acetic acid to yield the title compound.

E. 2,3-trans-5-[3-(tert-Butylamino)-2-hydroxypropoxy]-1,2,3,4-tetrahydro-2-hydroxy-3-methylamino-naphthalene and the 8-isomer A solution of trans-3-(methylamino)-5(and 8)-hydroxy-1,2,3,4-tetrahydro-2-naphthol and sodium methoxide is prepared in methanol and the solvent is removed in vacuo. The residue is dissolved in 80 ml of dimethylsulfoxide, ca. 10 ml distilled out at 0.2 mm, and the resulting solution is stirred overnight under nitrogen with epichlorohydrin. The bulk of the dimethylsulfoxide is removed in vacuo and the residue is partitioned between 400 ml each of water and chloroform. The aqueous layer is washed with two 300 ml portions of chloroform and the combined organic layer is washed with three 250 ml portions of water, dried and evaporated to give trans-3-(methylamino)-5(and 8)-(2,3-epoxypropoxy)-1,2,3,4-tetrahydro-2-naphthol.

A solution of the above epoxide and t-butylamine is heated at 80° C ± 5° overnight in a small Parr bomb. Solvent removal and crystallization yields the title compound.

What is claimed is:

1. A compound having the structure

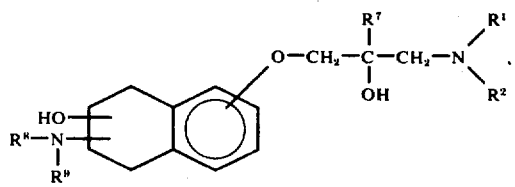

or a pharmaceutically acceptable salt thereof, wherein $R^1$, $R^2$, $R^8$ and $R^9$ are each independently selected from the group consisting of hydrogen, lower alkyl, and aryl-lower alkyl and $R^7$ is selected from the group consisting of hydrogen and methyl, and wherein lower alkyl refers to alkyl groups having up to 8 carbon atoms and aryl refers to phenyl or phenyl substituted with lower alkyl, halogen or nitro.

2. A compound in accordance with claim 1 wherein $R^1$ is hydrogen or lower alkyl and $R^2$ is lower alkyl.

3. A compound in accordance with claim 1 wherein $R^1$ is hydrogen and $R^2$ is lower alkyl.

4. A compound in accordance with claim 3 wherein $R^2$ is isopropyl.

5. A compound in accordance with claim 1 wherein $R^8$ is hydrogen.

6. The compound in accordance with claim 1 having the name 2,3-trans-5-[3-(isopropylamino)-2-hydroxypropoxy]-1,2,3,4-tetrahydro-3-(isopropylamino)-2-hydroxy-naphthalene.

7. A compound having the structure

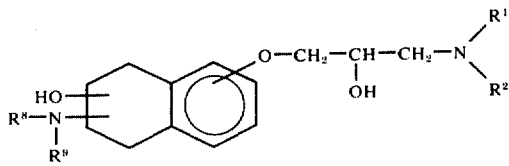

or a pharmaceutically acceptable salt thereof, wherein $R^1$, $R^2$, $R^8$ and $R^9$ are each independently selected from the group consisting of hydrogen, lower alkyl and aryl-lower alkyl, wherein lower alkyl refers to alkyl groups having up to 8 carbon atoms and aryl refers to phenyl or phenyl substituted with lower alkyl, halogen or nitro.

8. A compound in accordance with claim 7 wherein $R^1$ is hydrogen or lower alkyl and $R^2$ is lower alkyl.

9. A compound in accordance with claim 7 wherein $R^1$ is hydrogen and $R^2$ is lower alkyl.

* * * * *